United States Patent
Tsumaki et al.

(10) Patent No.: US 9,562,272 B2
(45) Date of Patent: Feb. 7, 2017

(54) SCREENING METHOD FOR THERAPEUTIC AGENT FOR CHONDROPATHY AND MODIFIED CHONDROCYTE FOR TREATMENT OF CHONDROPATHY

(75) Inventors: Noriyuki Tsumaki, Kyoto (JP); Hiroshi Takemori, Osaka (JP)

(73) Assignee: KYOTO UNIVERSITY, Kyoto (JP)

( * ) Notice: Subject to any disclaimer, the term of this patent is extended or adjusted under 35 U.S.C. 154(b) by 14 days.

(21) Appl. No.: 14/118,971

(22) PCT Filed: May 29, 2012

(86) PCT No.: PCT/JP2012/063709
§ 371 (c)(1),
(2), (4) Date: Feb. 6, 2014

(87) PCT Pub. No.: WO2012/165407
PCT Pub. Date: Dec. 6, 2012

(65) Prior Publication Data
US 2014/0212887 A1 Jul. 31, 2014

(30) Foreign Application Priority Data
May 31, 2011 (JP) .................................. 2011-121788

(51) Int. Cl.
| | |
|---|---|
| *G01N 33/48* | (2006.01) |
| *G01N 33/483* | (2006.01) |
| *G01N 33/487* | (2006.01) |
| *G01N 33/50* | (2006.01) |
| *G01N 33/53* | (2006.01) |
| *G01N 33/68* | (2006.01) |
| *C12Q 1/68* | (2006.01) |
| *C12N 5/077* | (2010.01) |
| *C12Q 1/48* | (2006.01) |

(52) U.S. Cl.
CPC ............ *C12Q 1/6897* (2013.01); *C12N 5/0655* (2013.01); *C12Q 1/485* (2013.01); *C12N 2501/727* (2013.01); *G01N 2500/02* (2013.01); *G01N 2500/10* (2013.01)

(58) Field of Classification Search
None
See application file for complete search history.

(56) References Cited

U.S. PATENT DOCUMENTS

| | | | | |
|---|---|---|---|---|
| 5,874,209 | A | * 2/1999 | Karin et al. | ...................... 435/4 |
| 2006/0246418 | A1* | 11/2006 | Montminy | ........................ 435/4 |
| 2011/0189694 | A1* | 8/2011 | Woloszczuk et al. | ......... 435/7.1 |

FOREIGN PATENT DOCUMENTS

| | | |
|---|---|---|
| JP | 2002-51786 | 2/2002 |
| WO | 2010/046443 | 4/2010 |

OTHER PUBLICATIONS

SIK3 sequence. Accessed May 8, 2015 at http://www.uniprot.org/uniprot/Q9Y2K2.*
Jones et al., 2003, Pediatric Research 54:230-236.*
Richmond et al., 2010, Endocr. Dev. 18:92-108.*
Patent Cooperation Treaty (PCT) International Preliminary Report on Patentability issued Dec. 2, 2013 in International Application No. PCT/JP2012/063709.
International Search Report issued Aug. 14, 2012 in International (PCT) Application No. PCT/JP2012/063709.
Lin et al., "Modulating hedgehog signaling can attenuate the severity of osteoarthritis", Nature Medicine, vol. 15, No. 12, Dec. 2009, pp. 1421-1425.
Saito et al., "Transcriptional regulation of endochondral ossification by HIF-2α during skeletal growth and osteoarthritis development", Nature Medicine, vol. 16, No. 6, Jun. 2010, pp. 678-686.
Yang et al., "Hypoxia-inducible factor-2α is a catabolic regulator of osteoarthritic cartilage destruction", Nature Medicine, vol. 16, No. 6, Jun. 2010, pp. 687-693.
Yuasa et al., "Transient Activation of Wnt/β-Catenin Signaling Induces Abnormal Growth Plate Closure and Articular Cartilage Thickening in Postnatal Mice", The American Journal of Pathology, vol. 175, No. 5, Nov. 2009, pp. 1993-2003.
Pelttari et al., "Premature Induction of Hypertrophy During In Vitro Chondrogenesis of Human Mesenchymal Stem Cells Correlates With Calcification and Vascular Invasion After Ectopic Transplantation in SCID Mice", Arthritis & Rheumatism, vol. 54, No. 10, Oct. 2006, pp. 3254-3266.
Warman et al., "Nosology and Classification of Genetic Skeletal Disorders: 2010 Revision", American Journal of Medical Genetics, vol. 155, No. 5, May 2011, pp. 943-968.
Japanese Office Action dated Jul. 14, 2015, issued in corresponding Japanese Patent Application No. 2011-121788.
Y. Katoh, et al., "Silencing the constitutive active transcription factor CREB by the LKB1-SIK signaling cascade", FEBS J., 2006, vol. 273, No. 12, pp. 2730-2748.
Yasuhito Yahara et al., "Pterosin B prevents chondrocyte hypertrophy and osteoarthritis in mice by inhibiting Sik3", Nature Communications, Nature Communication, 2016, 7:10959, doi: 10.1038/ncomms10959, pp. 1-12.

* cited by examiner

*Primary Examiner* — Elizabeth C Kemmerer
(74) *Attorney, Agent, or Firm* — Wenderoth, Lind & Ponack, L.L.P.

(57) ABSTRACT

The use of salt-inducible kinase 3 allows screening for a substance having an effect of increasing cartilage volume and/or an effect of normalizing chondrocyte differentiation. A modified chondrocyte in which the expression or function of salt-inducible kinase 3 gene is inhibited or enhanced can be used to ameliorate a disease associated with reduced cartilage volume and/or a disease associated with impaired cartilage growth.

8 Claims, 6 Drawing Sheets

US 9,562,272 B2

SCREENING METHOD FOR THERAPEUTIC AGENT FOR CHONDROPATHY AND MODIFIED CHONDROCYTE FOR TREATMENT OF CHONDROPATHY

TECHNICAL FIELD

The present invention relates to a screening method for a therapeutic agent for chondropathy and a modified chondrocyte for the treatment of chondropathy.

BACKGROUND ART

Osteoarthritis (OA) is a progressive degenerative joint disease characterized by the degeneration of articular cartilage and the growth and reconstitution of subchondral bone. The symptoms are stiffness, restriction of the movement, pain, and the like and the incidence is higher with increasing age. Due to little repair capacity of cartilage, there is no radical cure for osteoarthritis and current therapy is aimed to control pain by limiting exercise and using an analgesic. If the symptoms have progressed and the disease has reached the end stage, artificial joint replacement is performed to excise degenerative articular cartilage and cover the site with a metal cover.

In an attempt to develop a cartilage repair promoter, compounds or proteins for promoting the growth of chondrocytes have been searched for, but only bone morphogenetic proteins (BMPs) have been discovered as proteins that actually increase cartilage tissue. However, BMPs have the effect of, after increasing cartilage, hypertrophying the chondrocytes and replacing them with bone, which causes problems in use for the treatment of articular cartilage. In recent years, it has been pointed out that the acceleration of chondrocyte hypertrophy is involved in the degeneration of articular cartilage and consequently the prevention of chondrocyte hypertrophy has become one of the main targets in the treatment of osteoarthritis. Target molecules that have been identified until now include Hedgehog (Non Patent Literature 1) and Hif-2α (Non Patent Literature 2 and 3). It has been also reported that transient activation of β-catenin signaling induces thickening of articular cartilage (Non Patent Literature 4).

Regenerative medicine for the treatment of cartilage injury such as articular cartilage injury and growth plate injury caused by trauma, disturbance of blood circulation, or the like has also been studied using stem cell transplantation. However, cartilage-like cells induced from stem cells tend to hypertrophy, which poses problems (Non Patent Literature 5).

Chondrodysplasia, which is included in skeletal dysplasia, is a general term for various kinds of diseases that cause dwarfism, skeletal growth disorder, skeletal deformation, and the like due to congenital disorder of the cartilage primordium and the growth plate. Chondrodysplasia is often caused by mutations of various kinds of genes involved in chondrocyte differentiation (Non Patent Literature 6). The clinical conditions are related to the disorder of chondrocyte differentiation, which includes both cases where chondrocyte differentiation is enhanced and where chondrocyte differentiation is inhibited. Hypertrophy of chondrocytes is one aspect of chondrocyte differentiation. There has been desired the development of a drug capable of controlling chondrocyte differentiation as a therapeutic agent for chondrodysplasia. Another possibility is a therapy in which chondrocytes are implanted so as to normalize the growth of some of the growth plates in chondrodysplasia patients.

CITATION LIST

Non Patent Literature

Non Patent Literature 1:
Lin A C, et al. Nat Med. 2009; 15: 1421-1425.
Non Patent Literature 2:
Saito T, et al. Nat Med. 2010; 16: 678-686.
Non Patent Literature 3:
Yang S, et al. Nat Med. 2010; 16: 687-693.
Non Patent Literature 4:
Yuasa T, et al. Am J Pathol. 2009; 175: 1993-2003.
Non Patent Literature 5:
Pelttari K, et al. Arthritis Rheum. 2006; 54: 3254-3266.
Non Patent Literature 6:
Warman M L, et al. Am J Med Genet A. 2011 May; 155(5): 943-68.

SUMMARY OF INVENTION

Technical Problem

An object of the present invention is to discover a molecule involved in the differentiation or hypertrophy of chondrocytes and provide a screening method for a therapeutic agent for chondropathy. Another object of the present invention is to provide a modified chondrocyte that can be used for the treatment of chondropathy and for the analysis of the clinical conditions of chondropathy.

Solution to Problem

The present invention includes the following aspects for achieving the above objects.
[1] A screening method for a substance having an effect of increasing cartilage volume and/or an effect of normalizing chondrocyte differentiation, the method comprising using salt-inducible kinase 3.
[2] A modified chondrocyte in which the expression or function of salt-inducible kinase 3 is inhibited or enhanced, for use in the amelioration of a disease associated with reduced cartilage volume and/or a disease associated with impaired cartilage growth.

Advantageous Effects of Invention

The screening method of the present invention allows screening for a substance useful as a therapeutic agent for a disease associated with reduced cartilage volume and/or a disease associated with impaired cartilage growth. The modified chondrocyte of the present invention is useful for the amelioration of a disease associated with reduced cartilage volume and/or a disease associated with impaired cartilage growth. The modified chondrocyte of the present invention can also be used, as a disease model cell that reproduces the disorder of chondrocyte differentiation, in the analysis of the clinical conditions of chondropathy and in the screening for a drug for chondropathy.

DESCRIPTION OF EMBODIMENTS

Figure 1:
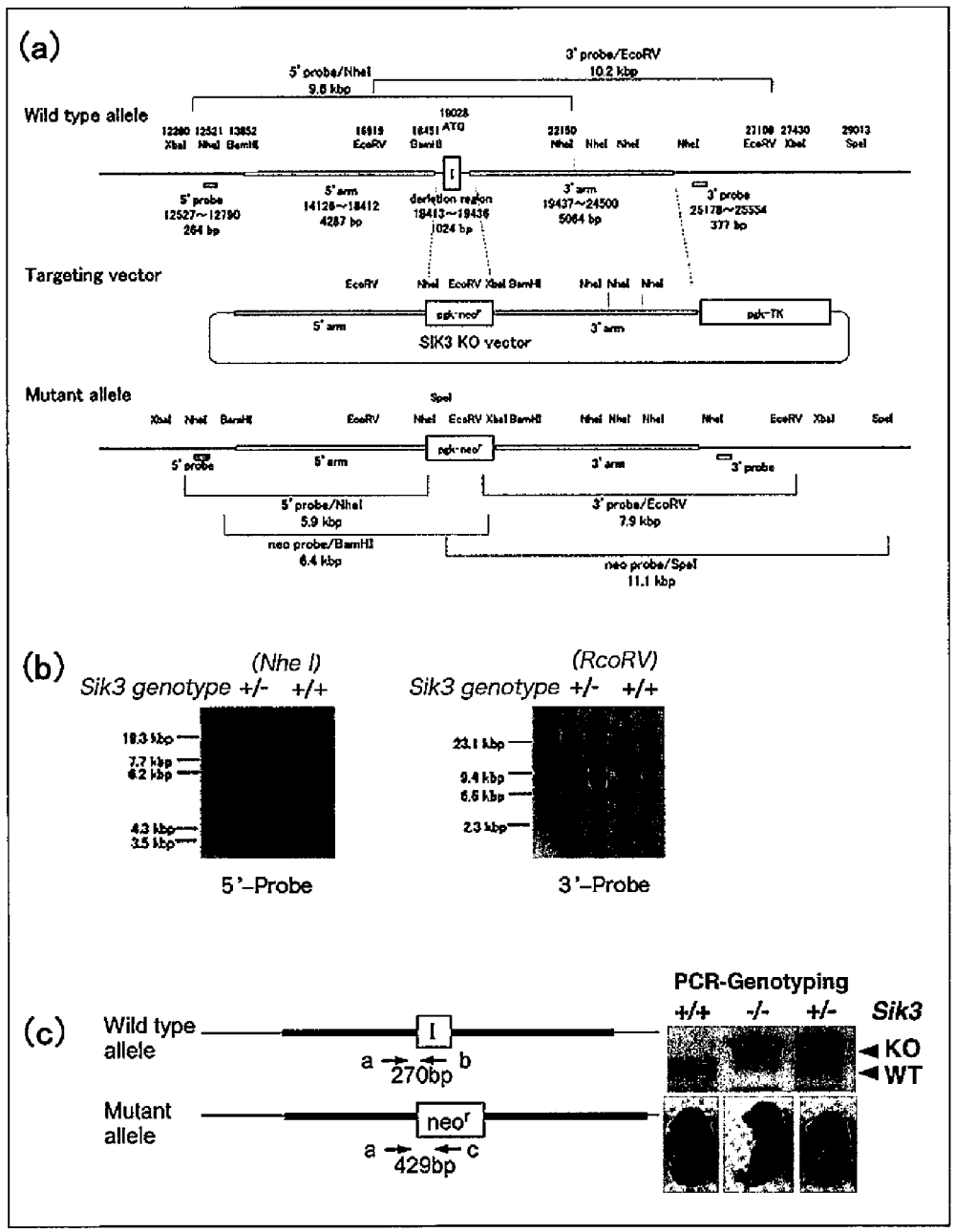
FIG. 1 (a) shows the constructs of a targeting vector for the generation of SIK3 knockout mice and of a wild-type allele and a mutant allele of the SIK3 gene. (b) shows the results of southern blot analysis of homologous recombinant ES cells and non-recombinant ES cells. (c) shows the results of PCR genotypic analysis of a newborn obtained by mating heterozygous mice having the mutant allele.

The inventors generated knockout mice deficient in salt-inducible kinase 3 (hereinafter referred to as "SIK3") and found that the mice showed remarkable inhibition of hypertrophy of growth-plate chondrocytes, an increase in articular cartilage volume, and thickening of articular cartilage tissue. This phenotype is not observed in SIK2 knockout mice (Pigment Cell Melanoma Res. 2010: 23 809-819). For the purpose of confirming that the phenotype is due to the deficiency of SIK3, heterozygous mice with a mutant allele of the SIK3 gene were mated with SIK3 gene transgenic mice and the produced mice were subjected to a rescue test. As a result, F1 mice with SIK3 Tg SIK3$^{-/-}$ genotype showed the same phenotype as that of wild-type mice. These results demonstrated that the inhibition of the expression or function of SIK3 results in the inhibition of hypertrophy of chondrocytes and increase in cartilage volume.

The inventors also found that the growth plate of the knee joint of the SIK3 gene transgenic mice disappeared at an earlier stage than that of wild-type mice. Based on this finding, it was considered that enhancement of the expression or function of SIK3 would result in acceleration of chondrocyte hypertrophy and of endochondral ossification.

The above findings revealed that the use of SIK3 would allow screening for a substance useful as a therapeutic agent for chondropathy. Also revealed is that a chondrocyte in which the expression or function of SIK3 is inhibited and a chondrocyte in which the expression or function of SIK3 is enhanced would be useful for the amelioration or treatment of chondropathy.

Screening Method

The present invention provides a screening method for a substance useful as a therapeutic agent for chondropathy, the method comprising using SIK3. In particular, the present invention provides a screening method for a substance having an effect of increasing cartilage volume and/or an effect of normalizing chondrocyte differentiation, the method comprising using SIK3. The effect of normalizing chondrocyte differentiation includes an effect of normalizing chondrocyte differentiation by increasing the speed of chondrocyte differentiation when the speed is lower than normal and an effect of normalizing chondrocyte differentiation by reducing the speed of chondrocyte differentiation when the speed is higher than normal.

The screening for a substance having an effect of increasing cartilage volume and a substance having an effect of reducing the speed of chondrocyte differentiation can be achieved by selecting a test substance that inhibits the expression or function of SIK3. In contrast, the screening for a substance having an effect of increasing the speed of chondrocyte differentiation can be achieved by selecting a test substance that enhances the expression or function of SIK3.

SIK will be described below. SIK1 (salt-inducible kinase 1) is a protein kinase isolated from the adrenal cortex of rats fed with a high salt diet as a candidate for a blood pressure-regulating factor. There are two types of other protein kinases similar to SIK1 and they are named SIK2 and SIK3 (hereinafter, when matters common to SIK1/2/3 are described, SIK1/2/3 is merely referred to as SIK). The significant role of the SIK signaling cascade is feedback repression on the transcription factor CREB, which is activated by cAMP (JBC 2002: 277 15629-37 and Cell 2004: 11461-76). CREB does not exhibit any transcriptional activity in the absence of a transcription coupling factor named TORC (transducer of regulated CREB activity). SIK represses CREB by inactivating TORC in a phosphorylation-dependent manner. Known physiological roles of SIK are the inhibition of CREB-dependent hepatic gluconeogenesis by SIK1 and SIK2 (Nature 2005:437 1109-11), the inhibition of CREB-dependent pancreatic insulin secretion by SIK2 (Cell 2004:11461-76), the inhibition of CREB-dependent expression of a brain-derived neurotrophic factor (BDNF) in the brain (Neuron 2011:69 106-119), and the like. SIK1 is also reported to enhance transcription that depends on MEF2C etc. by inhibiting class II HDAC (histone deacetylase) (Nat Med 2007: 13 597-603). The physiological significance of SIK3, however, has not been clarified and the analysis of knockout mice or transgenic mice has been awaited.

SIK3, which is the target of the screening method of the present invention, is not particularly limited and may be derived from any kinds of organisms. Preferably, SIK3 is derived from a mammal. The mammal is preferably a human, a chimpanzee, a monkey, a dog, a cattle, a mouse, a rat, a guinea pig, or the like, and is more preferably a human. The base sequences of the SIK3-encoding genes of various kinds of animals and the amino acid sequences thereof can be obtained from a known database (DDBJ, GenBank, EMBL, etc.) with, for example, the accession numbers shown in Table 1.

TABLE 1

|  | Base sequence | Amino acid sequence |
|---|---|---|
| Human | NM_025164 | NP_079440 |
| Chimpanzee | XM_508771 | XP_508771 |
| Dog | XM_536563 | XP_536563 |
| Cattle | XM_582999 | XP_582999 |
| Mouse | NM_027498 | NP_081774 |

A test substance to be subjected to the screening method of the present invention is, for example, a nucleic acid, a peptide, a protein, a non-peptidic compound, a synthetic compound, a fermentation product, a cell extract, a cell culture supernatant, a plant extract, a mammalian tissue extract, a plasma, or the like. The test substance may be a novel substance or a known substance. The test substance may be in the form of a salt and the salt may be a salt with a physiologically acceptable acid or base.

A substance obtainable by the screening method of the present invention is useful as an active ingredient of a therapeutic agent for various chondropathies. Examples of chondropathies include osteoarthritis, cartilage injury, and chondrodysplasia. Chondrodysplasia includes achondroplasia, dyschondroplasia, chondrodystrophy, dyschondrogenesis, enchondromatosis, etc. Among these, osteoarthritis and cartilage injury are diseases associated with reduced cartilage volume. Chondrodysplasia is a disease associated with impaired cartilage growth. Among the diseases included in chondrodysplasia, for example, achondroplasia is considered to be a disease associated with enhanced chondrocyte differentiation (Deng C, et al. Cell. 1996 Mar. 22; 84 (6): 911-21, Minina E, et al. Dev Cell. 2002 September; 3 (3): 439-49, and Dailey L, et al. J Cell Biol. 2003 Jun. 23; 161 (6): 1053-66). Also among the diseases included in chondrodysplasia, for example, Jansen-type metaphyseal chondrodysplasia is considered to be a disease associated with inhibited chondrocyte differentiation (Schipani E, et al. Science. 1995 Apr. 7; 268 (5207): 98-100).

A first embodiment of the screening method of the present invention is a screening method comprising the steps of bringing a test substance into contact with a cell expressing endogenous SIK3, measuring the amount of SIK3 protein or mRNA in the cell, and analyzing the test substance-dependent changes in the amount of the SIK3 protein or mRNA. The screening method of this embodiment can select a substance that inhibits the expression of SIK3 or a substance that enhances the expression of SIK3. The cell expressing endogenous SIK3 is not particularly limited as long as the cell expresses endogenous SIK3 and may be an in vivo cell or a cultured cell. Preferred is a cultured cell in terms of the ease of operation. The cultured cell may be a primary cultured cell or an established cell line. Specific examples of the cell line expressing endogenous SIK3 include HepG2, COS-7, ATDC5, etc. These cell lines are suitable to be used in the first embodiment of the screening method of the present invention.

The method for bringing a test substance into contact with a cell expressing endogenous SIK3 is not particularly limited and may be any method as long as the test substance can be brought into contact with the cell. In cases where a cultured cell is used, for example, a method in which a test substance is added to the medium may be used. In cases where a test substance is brought into contact with an in vivo cell, examples of the method include systemic administration such as oral administration, intravenous administration, and intraperitoneal administration; and local administration to a target organ or tissue. Preferably, a control group free from contact with any test substance is provided.

The amount of the SIK3 protein in a cell can be determined by a known protein quantitation method after extraction of the protein from the cell by a known method. Examples of the known protein quantitation method include Western blotting, EIA, ELISA, RIA, a method using a protein quantitation reagent, and the like. The amount of the SIK3 mRNA in a cell can be determined by a known mRNA quantitation method after extraction of the RNA from the cell by a known method. Examples of the known mRNA quantitation method include Northern blotting, RT-PCR, quantitative RT-PCR, RNase protection assay, and the like.

The method for analyzing the test substance-dependent changes in the amount of the SIK3 protein or mRNA is not particularly limited. For example, a test substance can be selected as a substance of interest when the amount of the SIK3 protein or mRNA in a cell brought into contact with the test substance is decreased or increased compared with that in a control group free from contact with the test substance. The degree of decrease or increase in the amount of the SIK3 protein or mRNA by the test substance is not particularly limited, but, for example, the test substance preferably decreases the amount of the protein or mRNA to 50% or less or increases the amount of the protein or mRNA to 150% or more compared with the amount in cells free from contact with the test substance, and more preferably the test substance decreases the amount of the protein or mRNA to 25% or less or increases the amount of the protein or mRNA to 175% or more.

A second embodiment of the screening method of the present invention is a screening method comprising the steps of bringing a test substance into contact with a cell that can be used for the determination of the promoter activity of SIK3, measuring the promoter activity of SIK3 in the cell, and analyzing the test substance-dependent changes in the promoter activity of SIK3. The screening method of this embodiment can select a substance that inhibits the expression of SIK3 or a substance that enhances the expression of SIK3. The cell that can be used for the determination of the promoter activity of SIK3 is, for example, a cell into which a vector containing a reporter gene fused downstream of a DNA fragment having the promoter activity of SIK3 has been introduced. The host cell is not particularly limited and examples thereof include HEK293, HepG2, COS-7, ATDC5, etc.

The base sequence of the promoter region of human SIK3 gene is shown in SEQ ID NO: 1. The base sequence of the promoter region of mouse SIK3 gene is shown in SEQ ID NO: 2. A DNA fragment having the same or substantially the same base sequence as the base sequence represented by SEQ ID NO: 1 and a DNA fragment having the same or substantially the same base sequence as the base sequence represented by SEQ ID NO: 2 are suitable for use as the above DNA fragment having the promoter activity of SIK3. The DNA fragment having the promoter activity of SIK3 is not limited to these, and a DNA fragment having the promoter region of the SIK3 gene derived from other organisms may be used.

The DNA fragment having substantially the same base sequence as the base sequence represented by SEQ ID NO: 1 or 2 may be any DNA fragment as long as it has a base sequence having homology of, for example, about 50% or more, preferably about 60% or more, further preferably about 70% or more, more preferably about 80% or more, particularly more preferably about 90% or more, most preferably about 95% or more to the base sequence represented by SEQ ID NO: 1 or 2, and has the same promoter activity as a DNA fragment having the base sequence represented by SEQ ID NO: 1 or 2.

The reporter gene is not particularly limited and may be any commonly used reporter gene, but preferred is a stable reporter gene whose activity is easy to quantify. Examples of such a reporter gene include a gene encoding luciferase, β-galactosidase, β-glucuronidase, chloramphenicol acetyltransferase, alkaline phosphatase, peroxidase, green fluorescent protein (GFP), or the like.

The method for bringing a test substance into contact with a cell that can be used for the determination of the promoter activity of SIK3 is not particularly limited and any method can be used as long as the test substance can be brought into contact with the cell. Examples of the method include a method in which a test substance is added to the medium. Preferably, a control group free from contact with any test substance is provided.

The promoter activity of SIK3 can be determined by measuring the expression of the reporter gene. The method for measuring the expression of the reporter gene is appropriately selected according to the protein encoded by the reporter gene (reporter gene product). For example, in cases where the reporter gene encodes luciferase, transfected cells are lysed by a suitable method, luciferin as a substrate is added to the supernatant of the cell lysate, and the luminescence is measured with a commercially available detector to determine the expression of the reporter gene. In cases where other reporter genes are used, the amount of a reporter gene product can also be measured by a known method.

The method for analyzing the test substance-dependent changes in the promoter activity of SIK3 is not particularly limited. For example, a test substance can be selected as a substance of interest when the promoter activity of SIK3 in a cell brought into contact with the test substance is decreased or increased compared with that in a control group free from contact with the test substance. The degree of decrease or increase in the promoter activity of SIK3 by the test substance is not particularly limited, but, for example, the test substance preferably decreases the promoter activity to 50% or less or increases the promoter activity to 150% or more compared with the activity in cells free from contact with the test substance, and more preferably the test substance decreases the promoter activity to 25% or less or increases the promoter activity to 175% or more.

A third embodiment of the screening method of the present invention is a screening method comprising the steps of bringing a test substance into contact with SIK3 and its substrate, measuring the binding of SIK3 to its substrate, and analyzing the test substance-dependent changes in the degree of the binding. The screening method of this embodiment can select a substance that inhibits the function of SIK3 or a substance that enhances the function of SIK3. The substrate for SIK3 may be any protein or peptide as long as the protein or peptide has the amino acid sequence represented by the formula (1) shown below, and the method described in, for example, Cell. 2004119: 61-74 or FEBS J. 2006 273: 2730-2748 can be used. Specific examples of the substrate include the above-mentioned TORC, HDAC, a fragment thereof (containing the amino acid sequence represented by the formula (1)), etc.

$$\text{Leu-}X_1\text{-}Y_1\text{-}Y_2\text{-}X_2\text{-Ser-}X_3\text{-}X_4\text{-}X_5\text{-Leu} \quad (1)$$

(In the formula, $X_1$, $X_2$, $X_3$, $X_4$, and $X_5$ are each the same or different and represent any given amino acid residue, $Y_1$ represents Arg or Lys, and $Y_2$ represents Ser or Thr.)

SIK3 recognizes a protein having the amino acid sequence represented by the formula (1) as its substrate, binds to the protein, and phosphorylates Ser at position 6 of the amino acid sequence. In the amino acid sequence represented by the formula (1), Leu at position 1 and Leu at position 10 may be substituted with another hydrophobic amino acid.

The SIK3 used in the screening method of this embodiment may be a naturally occurring protein or a recombinant protein. For example, the SIK3 can be obtained by a known method (for example, a method using an affinity column) from the culture supernatant or cell extract of a cell expressing endogenous SIK3 or of a cell into which a SIK3 expression vector has been introduced. The substrate for the SIK3 may also be a naturally occurring protein or recombinant protein, and as in the case of the SIK3, the substrate can be obtained by a known method. For example, the amino acid sequence of TORC and the base sequence of a gene encoding TORC can be obtained from a known database (DDBJ, GenBank, EMBL, etc.). The accession number of the amino acid sequence of human TORC2 is NP_859066 and the accession number of the base sequence of the gene encoding the amino acid sequence is NM_181715. In the amino acid sequence of human TORC2 (693 amino acids, SEQ ID NO: 3), the above sequence of the formula (1) is present in position 166 to 175.

The method for bringing a test substance into contact with SIK3 and its substrate is not particularly limited, and examples thereof include a method in which a reaction system containing SIK3 and its substrate is prepared and then a test substance is added thereto. The contact duration and the contact temperature are not particularly limited and may be selected as appropriate. Preferably, a control group free from contact with any test substance is provided.

The method for measuring the binding of SIK3 to its substrate is not particularly limited and may a known method selected as appropriate. For example, ELISA can be suitably used. In cases where the screening method of this embodiment is performed using ELISA, either SIK3 or its substrate is immobilized, non-immobilized SIK3 or its substrate and a test substance are added and reacted, and the binding of SIK3 to its substrate is detected using suitable primary and secondary antibodies.

The method for analyzing the test substance-dependent changes in the degree of the binding is not particularly limited. For example, a test substance can be selected as a substance of interest when the binding of SIK3 to its substrate under the condition of contact with the test substance is decreased or increased compared with that in a control group free from contact with the test substance. The degree of decrease or increase in the binding of SIK3 to its substrate by the test substance is not particularly limited, but, for example, the test substance preferably decreases the binding of SIK3 to its substrate to 50% or less or increases the binding of SIK3 to its substrate to 150% or more compared with the binding under the condition of free from contact with the test substance, and more preferably the test substance decreases the binding to 25% or less or increases the binding to 175% or more.

A fourth embodiment of the screening method of the present invention is a screening method comprising the steps of bringing a test substance into contact with SIK3 and its substrate, measuring the phosphorylation of the substrate for SIK3, and analyzing the test substance-dependent changes in the degree of the phosphorylation. The screening method of this embodiment can select a substance that inhibits the function of SIK3 or a substance that enhances the function of SIK3.

In this embodiment, the same SIK3 and the same substrate for SIK3 as in the third embodiment can be used, and a test substance can be brought into contact with these in the same manner. The method for measuring the phosphorylation of the substrate for SIK3 is not particularly limited and may be a known method selected as appropriate. For example, a method using an antibody capable of recognizing phosphorylation can be used. In this embodiment, in cases where the above human TORC2 is used as the substrate for SIK3, the antibody used in the method is an antibody that specifically recognizes a protein having the amino acid sequence of human TORC2 (SEQ ID NO: 3) in which serine at position 171 is phosphorylated. Such an antibody can be obtained in accordance with a known preparation method for a polyclonal antibody or monoclonal antibody using, as an immunogen, a protein in which serine at position 171 of human TORC2 is phosphorylated or a peptide containing the phosphorylation site. Such a method is described in, for example, Japanese Patent No. 4568022.

The method for analyzing the test substance-dependent changes in the degree of the phosphorylation is not particularly limited. For example, a test substance can be selected as a substance of interest when the phosphorylation of the substrate for SIK3 under the condition of contact with the test substance is decreased or increased compared with that in a control group free from contact with the test substance. The degree of decrease or increase in the phosphorylation of the substrate for SIK3 by the test substance is not particularly limited, but, for example, the test substance preferably decreases the phosphorylation to 50% or less or increases the phosphorylation to 150% or more compared with the phosphorylation under the condition of free from contact with the test substance, and more preferably the test substance decreases the phosphorylation to 25% or less or increases the phosphorylation to 175% or more.

A fifth embodiment of the screening method of the present invention is a screening method comprising the steps of adding a test substance to a system capable of evaluating signal transduction activity mediated by SIK3, measuring the signal transduction activity mediated by SIK3, and analyzing the test substance-dependent changes in the signal transduction activity. The screening method of this embodiment can select a substance that inhibits the function of SIK3 or a substance that enhances the function of SIK3. The system capable of evaluating the signal transduction activity mediated by SIK3 is not particularly limited and may be any system capable of evaluating the differences in the downstream signal transduction activity between the condition where the SIK3 activity is normal and the condition where the SIK3 activity is inhibited or enhanced. For example, a system in which the expression of a reporter gene varies between the condition where the SIK3 activity is normal and the condition where the SIK3 activity is inhibited or enhanced may be constructed and used for the screening method. Specific examples of the system include the one used in Example 1 described later (a system using a vector expressing a substrate for SIK3 and a cell into which a vector containing a reporter gene linked to a promoter to be activated by the phosphorylation of the substrate has been introduced).

The method for measuring the signal transduction activity mediated by SIK3 may be a known method selected as appropriate in accordance with the evaluation system used. For example, in cases where the evaluation system uses a reporter gene, the amount of the reporter gene product is measured by a known method selected in accordance with the reporter gene used.

The method for analyzing the test substance-dependent changes in the signal transduction activity is not particularly limited. For example, a test substance can be selected as a substance of interest when the activity of SIK3 under the condition of contact with the test substance is decreased or increased compared with that in a control group free from contact with the test substance. The degree of decrease or increase in the activity of SIK3 by the test substance is not particularly limited, but, for example, the test substance preferably decreases the activity to 50% or less or increases the activity to 150% or more compared with the activity under the condition of free from contact with the test substance, and more preferably the test substance decreases the activity to 25% or less or increases the activity to 175% or more.

Drugs Containing a Substance Obtained by Screening

The substance obtained by the screening method of the present invention has an effect of increasing cartilage volume and/or an effect of normalizing chondrocyte differentiation and is therefore useful as an active ingredient of a therapeutic agent for various chondropathies. Examples of chondropathies include osteoarthritis, cartilage injury, and chondrodysplasia. Consequently, the present invention includes a therapeutic drug for chondropathies, the drug comprising, as an active ingredient, a substance that inhibits the expression or function of SIK3 or a substance that enhances the expression or function of SIK3. The "substance having an effect of increasing cartilage volume" herein refers to a substance that, when administered to a normal individual, exerts an effect of increasing cartilage volume in the administration site (for example, the joints of the forelimbs and hindlimbs) compared with that in the same site of a normal individual to which the substance has not been administered. A method for confirming whether cartilage volume is increased is not particularly limited and the confirmation can be performed by, for example, preparing cartilage tissue specimens for comparison and observing the specimens under a microscope.

A substance obtainable by the screening method of the present invention, when to be used as a therapeutic agent for chondropathy, can be formulated into a pharmaceutical preparation by a conventional method. Pharmaceutical preparations for oral administration include, for example, solid or liquid dosage forms, in particular, a tablet (including a sugar-coated tablet and a film-coated tablet), a pill, a granule, a powder, a capsule (including a soft capsule), a syrup, an emulsion, a suspension, etc. These pharmaceutical preparations are produced by a known method and they may contain a carrier, a diluent, and/or an excipient that is usually used in the pharmaceutical field. Examples of the carrier or excipient for a tablet include lactose, starch, sucrose, magnesium stearate, etc. Pharmaceutical preparations for parenteral administration include, for example, an injection, a suppository, etc. Examples of the injection include dosage forms such as an intravenous injection, a hypodermic injection, an intradermal injection, an intramuscular injection, an intravenous drip infusion, and an intraarticular injection. Such an injection is prepared in accordance with a known method, for example, by dissolving, suspending, or emulsifying the above substance that inhibits the expression or function of SIK3 or a salt thereof into an aseptic aqueous or oily liquid usually used for an injection. The aqueous liquid for an injection is, for example, physiological saline, an isotonic solution containing glucose other auxiliary agents, and/or the like, and may be used in combination with a suitable solubilizing agent such as an alcohol (e.g., ethanol etc.), a polyalcohol (e.g., propylene glycol, polyethylene glycol, etc.), and a nonionic surfactant (e.g., polysorbate 80, HCO-50, etc.). The oily liquid is, for example, a sesame oil, a soybean oil, or the like, and may be used in combination with a solubilizing agent such as benzyl benzoate and benzyl alcohol. A suppository for rectal administration is prepared by mixing the above substance that inhibits the expression or function of SIK3 or a salt thereof with a usual base for a suppository.

Thus obtained pharmaceutical preparations are safe and low toxic and therefore can be orally or parenterally administered to, for example, a human or a warm blooded animal (e.g., mouse, rat, rabbit, sheep, pig, cattle, horse, bird, cat, dog, monkey, chimpanzee, etc.).

Modified Chondrocyte

The present invention provides a modified chondrocyte in which the expression or function of SIK3 is inhibited and a modified chondrocyte in which the expression or function of SIK3 is enhanced. These modified chondrocytes can be used to ameliorate a disease associated with reduced cartilage volume and/or a disease associated with impaired cartilage growth. Examples of the disease associated with reduced cartilage volume include osteoarthritis, cartilage injury, etc. and examples of the disease associated with impaired cartilage growth include chondrodysplasia etc. Specifically, for example, the modified chondrocyte in which the expression or function of SIK3 is inhibited can inhibit the maturation and degeneration of chondrocytes, thereby maintaining the morphology of chondrocytes, and is thus very useful as a cell used for regenerative medicine of a disease associated with reduced cartilage volume. In addition, for example, the modified chondrocyte in which the expression or function of SIK3 is inhibited is very useful as a cell used for transplantation to the growth plate of a patient with chondrodysplasia in which chondrocyte differentiation is enhanced, and the modified chondrocyte in which the expression or function of SIK3 is enhanced is very useful as a cell used for transplantation to the growth plate of a patient with chondrodysplasia in which chondrocyte differentiation is inhibited. Further, for example, the modified chondrocyte in which the expression or function of SIK3 is inhibited or enhanced is very useful as a disease model cell for the analysis of the clinical conditions of chondrodysplasia or for screening for a drug for chondrodysplasia.

The modified chondrocyte of the present invention in which the expression or function of SIK3 is inhibited can be obtained by, for example, modifying the SIK3 gene of a cell that can be induced to differentiate into a chondrocyte so that the SIK3 gene is inactivated, and inducing the cell to differentiate into a chondrocyte. Alternatively, the modified chondrocyte can be obtained by, for example, introducing siRNA, shRNA, or an antisense oligonucleotide into a chondrocyte. Alternatively, the modified chondrocyte can be obtained by, for example, harvesting a chondrocyte from a SIK3 knockout mouse (see Reference Example 1).

The modified chondrocyte of the present invention in which the expression or function of SIK3 is enhanced can be obtained by, for example, introducing a SIK3 expression vector into cells that can be induced to differentiate into chondrocytes, selecting a cell in which the expression of SIK3 is enhanced, and inducing the cell to differentiate into a chondrocyte. Alternatively, the modified chondrocyte can be obtained by, for example, introducing a SIK3 expression vector into chondrocytes and selecting a chondrocyte in which the expression of SIK3 is enhanced. Alternatively, the modified chondrocyte can be obtained by, for example, harvesting a chondrocyte from a SIK3 gene transgenic mouse (see Reference Example 2).

A suitable production method for the modified chondrocyte of the present invention in which the expression or function of SIK3 is inhibited is, for example, a method comprising the steps of modifying the SIK3 gene of a cell that can be induced to differentiate into a chondrocyte so that the SIK3 gene is inactivated, and inducing the obtained cell to differentiate into a chondrocyte. Examples of the cell that can be induced to differentiate into a chondrocyte include a stem cell, an immature chondrocyte, etc. The stem cell refers to a cell with self-renewal ability and pluripotency and includes a somatic stem cell, a pluripotent stem cell, etc. A somatic stem cell that can be induced to differentiate into a chondrocyte is, for example, a mesenchymal stem cell. Other examples of the somatic stem cell that can be induced to differentiate into a chondrocyte include an ES cell (embryonic stem cell), an iPS cell (induced pluripotent stem cell), a mGS cell (multipotent germline stem cell), a somatic cell fused with an ES cell, etc. Preferred are a mesenchymal stem cell, an ES cell, and an iPS cell.

The method for modifying the SIK3 gene is not particularly limited and may be a known genetic modification method selected as appropriate. Examples of the method include introduction of a random mutation using ultraviolet rays or a mutagen, introduction of a site-specific mutation, introduction of a mutation using a targeting vector, etc. The targeting vector used to destroy the SIK3 gene is, for example, the targeting vector that the inventors used for the preparation of SIK3 knockout mice (see FIG. 1 (a)). The inactivation of the SIK3 gene can be confirmed by, for example, measuring the amount of SIK3 mRNA or protein in a cell with a modified SIK3 gene, or measuring the kinase activity of SIK3 protein isolated from a cell with a modified SIK3 gene.

A suitable method for inducing the obtained cell to differentiate into a chondrocyte is, for example, the method described in J Clin Invest. 2011 121: 640-57.

EXAMPLES

The present invention will be illustrated in more detail below with reference to Reference Examples and Example, but the present invention is not limited thereto.

Reference Example 1

Analysis of Chondrocyte Differentiation in SIK3 Knockout Mice (1) SIK3 Knockout Mice (Hereinafter Referred to as "SIK3 KO Mice")

A targeting vector carrying, in consecutive order from the 5' end to 3' end, the 5'-end genome sequence of the mouse SIK3 gene (5' arm), a pgk promoter, a neomycin resistance gene, and the 3'-end genome sequence of the mouse SIK3 gene (3' arm) (see FIG. 1 (a)) was generated in accordance with a usual method. The obtained targeting vector was introduced into mouse ES cells and the cells were cultured in G418-containing medium to generate neomycin-resistant ES cells. DNA was extracted from the obtained neomycin-resistant ES cells and homologous recombinant clones were identified by southern blot analysis (see FIG. 1 (b)).

The obtained homologous recombinant clones were microinjected into blastocysts obtained from BDF2 mice, and the manipulated blastocysts were implanted into the womb of mice. The mice that conceived after the implantation gave birth to chimera mice. The chimera mice were mated with C57BL/6 mice to generate heterozygous mice with a mutant allele (hereinafter referred to as "SIK3 hetero KO mice"). The SIK3 hetero KO mice were mated to generate homozygous SIK3 KO mice. The genotype of the fetuses or the newborns was confirmed by PCR using the genomic DNA extracted from the tail, ear, or part of the skin. The following three types of primers were used for the PCR. A 270-bp band derived from the wild-type allele is amplified from the primers a and b, and a 429-bp band derived from the mutant allele is amplified from the primers a and c (see FIG. 1 (c)). The SIK3 hetero KO mice are available from the National Institute of Biomedical Innovation.

(SEQ ID NO: 4)
Primer a: 5'-GCTACCAACTTGGTTACAGTTGCT-3'

(SEQ ID NO: 5)
Primer b: 5'-AAAACGTCGAGGGTCAGCAGCAACTTCTAA-3'

(SEQ ID NO: 6)
Primer c: 5'-ACGAGACTAGTGAGACGTGCTACTTCCATT-3'

(2) Harvest of Limb Buds from Fetuses

The SIK3 hetero KO mice were mated and, after a predetermined time passed from the observation of mating behavior, pregnant mice were euthanized by carbon dioxide inhalation to produce 14.5-day post-coitum embryos (14.5 dpc) and 18.5-day post-coitum embryos (18.5 dpc). The limb buds of the fetuses were harvested and fixed in formalin.

(3) Harvest of Forelimbs and Hindlimbs from Mice after Birth

Three-month-old SIK3 KO mice and wild-type (WT) mice from the same brood were euthanized by carbon dioxide inhalation and dissected for harvesting the forelimbs and hindlimbs. The harvested limbs were fixed in formalin and then decalcified in EDTA.

(4) Tissue Specimen Preparation

One of the forelimbs and hindlimbs that were harvested and fixed was embedded in paraffin and sectioned at 5 μm. The sections were mounted on glass slides, deparaffinized, and then subjected to safranin O-fast green-iron hematoxylin staining. Cartilage matrix is stained red to orange with safranin O.

(5) Observation of Specimens

Figure 2:
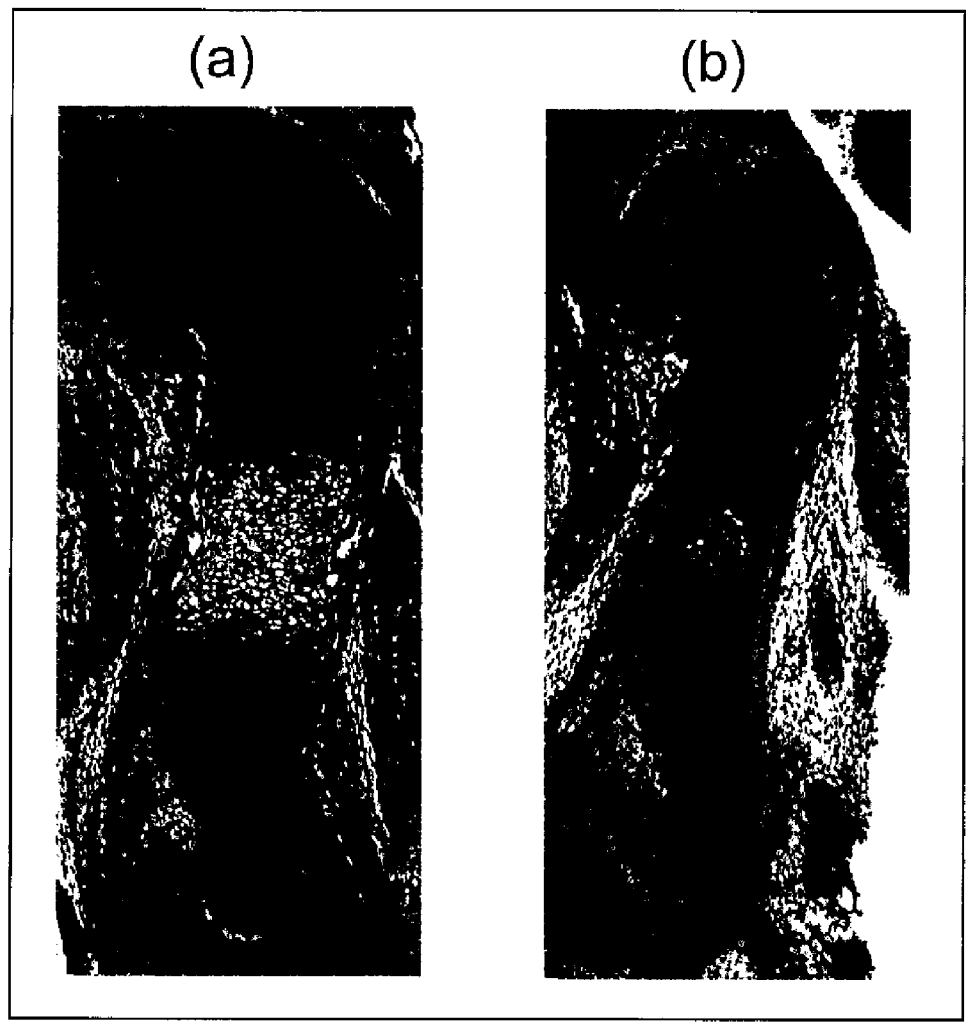
FIG. 2 shows histologically stained sections including the thighbone of a 14.5 dpc embryo obtained by mating heterozygous mice having a mutant allele of the SIK3 gene. (a) is a histologically stained section of a wild-type mouse and (b) is a histologically stained section of a SIK3 knockout mouse.

The obtained specimens were observed under an optical microscope. FIGS. 2 (a) and (b) show the histologically stained sections including the thighbone of the 14.5 dpc embryos. (a) is the wild-type mouse and (b) is the SIK3 KO mouse. In the figures, nonhypertrophied chondrocytes were strongly stained in the thighbone. As is apparent from FIGS. 2 (a) and (b) of the 14.5 dpc embryos, (a) the wild-type mouse showed chondrocyte hypertrophy in the center of the thighbone and this part is weakly stained, whereas the center of the thighbone of (b) the KO mouse was stained almost as strongly as the remaining part, which revealed that chondrocyte hypertrophy was inhibited.

Figure 3:
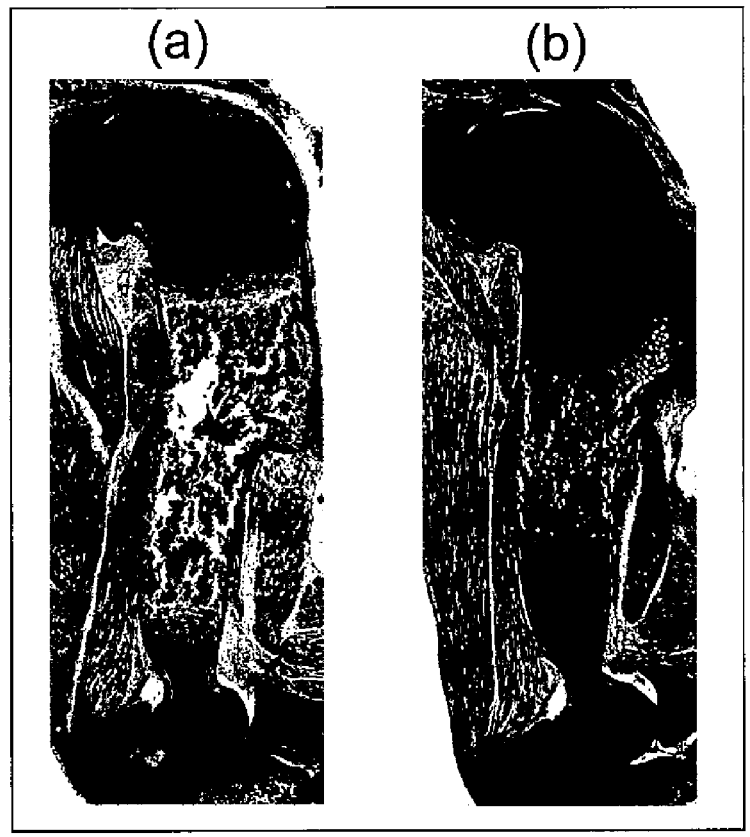
FIG. 3 shows histologically stained sections including the thighbone of a 18.5 dpc embryo obtained by mating heterozygous mice having a mutant allele of the SIK3 gene. (a) is a histologically stained section of a wild-type mouse and (b) is a histologically stained section of a SIK3 knockout mouse.

FIGS. 3 (a) and (b) show histologically stained sections including the thighbone of the 18.5 dpc embryos. (a) is the wild-type mouse and (b) is the SIK3 KO mouse. As is apparent from FIGS. 3 (a) and (b), the wild-type mouse (a) showed progressed ossification in the center of the thighbone, whereas the KO mouse (b) showed prolonged inhibition of chondrocyte hypertrophy and no occurrence of ossification.

Figure 4:
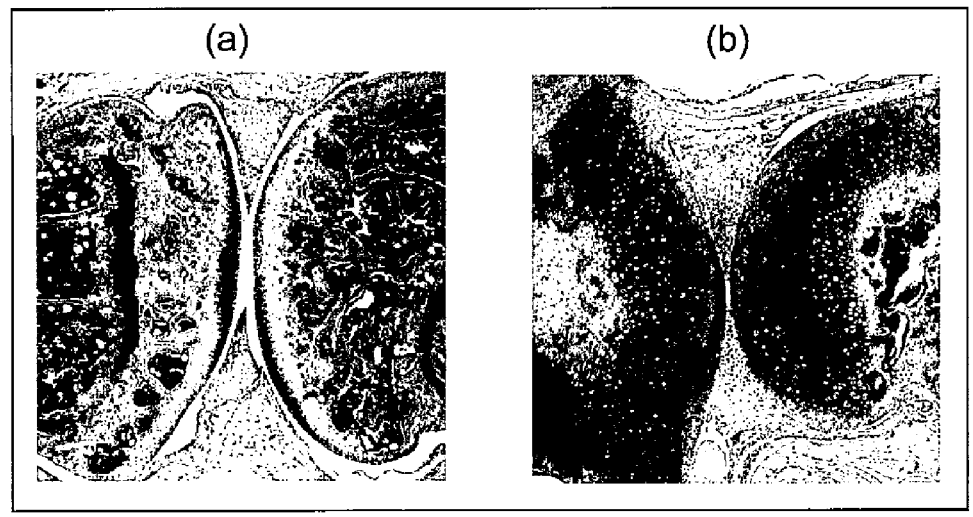
FIG. 4 shows histologically stained sections including the knee joint of a 3-month-old mouse obtained by mating heterozygous mice having a mutant allele of the SIK3 gene. (a) is a histologically stained section of a wild-type mouse and (b) is a histologically stained section of a SIK3 knockout mouse.

FIGS. 4 (a) and (b) show histologically stained sections including the knee joint of 3-month-old mice. (a) is the wild-type mouse and (b) is the SIK3 KO mouse. As is apparent from FIGS. 4 (a) and (b), the articular cartilage of the KO mouse (b) was significantly hypertrophied as compared with that of the wild-type mouse (a).

The above results, in which the inhibition of chondrocyte hypertrophy and the thickening of articular cartilage were observed in the SIK3 KO mice, suggest that SIK3 is a potential target for the inhibition of chondrocyte hypertrophy and of the thickening of cartilage.

Reference Example 2

Rescue Test Using SIK3 Transgenic Mice (1) SIK3 Transgenic Mice (Hereinafter Referred to as "SIK3 Tg Mice")

A transgene construct was generated by linking a human SIK3 cDNA (Accession No. NM_025164) to a promoter/enhancer for the α2(XI) collagen chain gene (Col11a2), which directs cartilage-specific expression (Tsumaki N, et al. J Cell Biol. 1996; 134: 1573-1582). This transgene insertion was cut from the vector backbone, purified, and then microinjected into mouse fertilized eggs. The eggs were implanted into the oviduct of pseudo-pregnant mice. From the mice produced from the pseudo-pregnant mice, SIK3 Tg mice were selected and thus a SIK3 Tg mouse line was established. The genotype of the fetuses or the newborns was confirmed by PCR using the genomic DNA extracted from the tail or ear tissue. The following primers were used for the PCR.

(SEQ ID NO: 7)
Forward primer: 5'-GATGTCGGATGCAGTTCTC-3'

(SEQ ID NO: 8)
Reverse primer: 5'-ATGTCTGTAATACACGTAGATGGATA-3'

(2) Test Method

The SIK3 hetero KO mice were mated with the SIK3 Tg mice and, 15.5 days after the observation of mating behavior, pregnant mice were euthanized by carbon dioxide inhalation to produce 15.5-day embryos (15.5 dpc). The genomic DNA was extracted from the skin of each fetus and the genotypes of the SIK3 knockout mice and the SIK3 transgenic mice were analyzed by PCR. The limb buds of the fetuses were harvested and fixed in formalin.

(3) Tissue Specimen Preparation

Sections were produced and stained in the same manner as in Reference Example 1.

(4) Observation of Specimens

Figure 5:
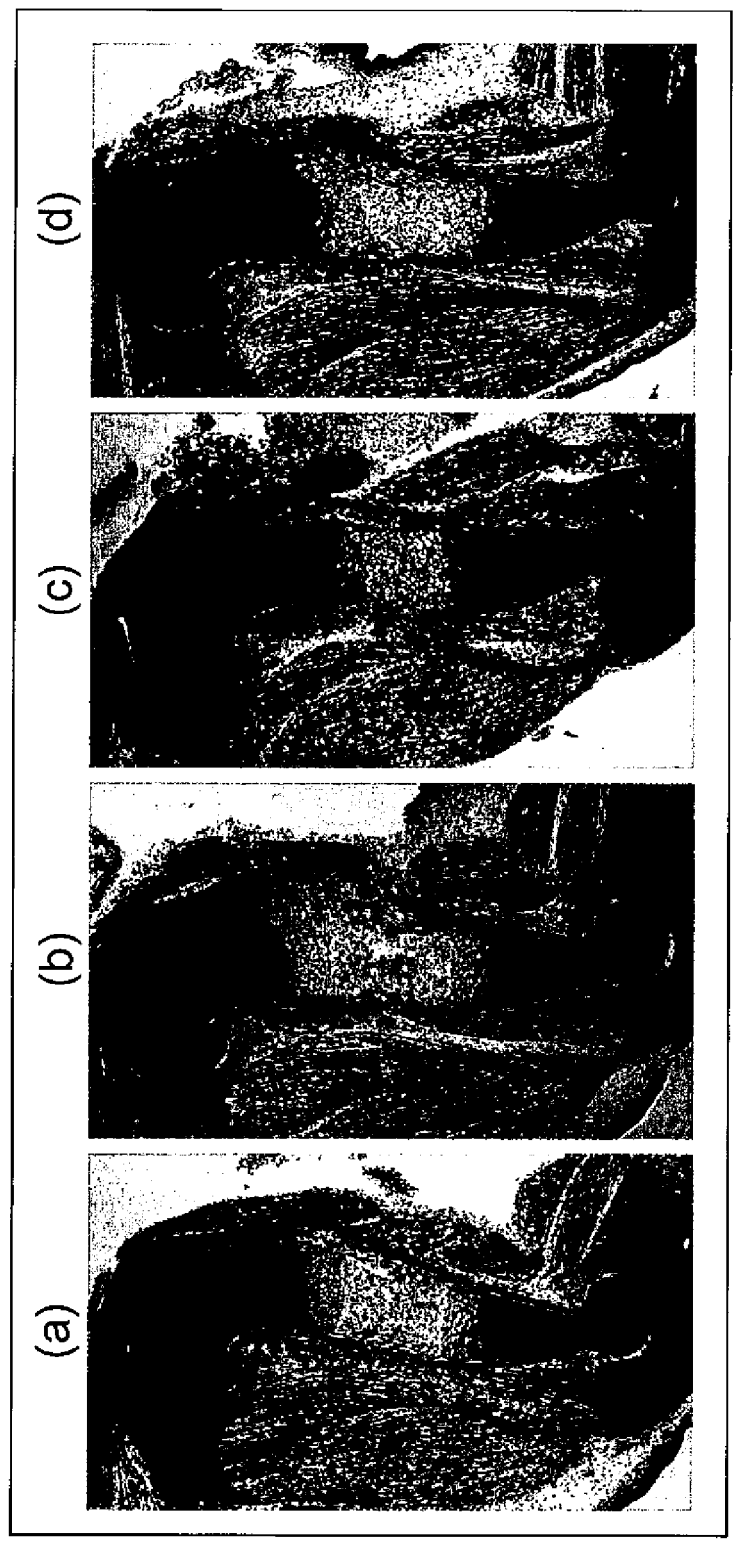
FIG. 5 shows histologically stained sections including the thighbone of 15.5 dpc embryos obtained by mating heterozygous mice having a mutant allele of the SIK3 gene with SIK3 gene transgenic mice. (a) is a histologically stained section of a mouse with SIK3 Tg SIK3$^{+/+}$ genotype, (b) is a histologically stained section of a mouse with SIK3 Tg SIK3$^{+/-}$ genotype, (c) is a histologically stained section of a mouse with SIK3$^{-/-}$ genotype, and (d) is a histologically stained section of a mouse with SIK3 Tg SIK3$^{-/-}$ genotype.

The obtained specimens were observed under an optical microscope. FIG. 5 (a) to (d) show the histologically stained sections including the thighbone of the 15.5 dpc embryos. (a) is a mouse with SIK3 Tg SIK3$^{+/+}$ genotype, (b) is a mouse with SIK3 Tg SIK3$^{-/-}$ genotype, (c) is a mouse with SIK3$^{-/-}$ genotype, and (d) is a mouse with SIK3 Tg SIK3$^{-/-}$ genotype. As is apparent from FIG. 5, (c) the mouse with SIK3$^{-/-}$ genotype (SIK3 KO mouse) showed the inhibition of chondrocyte hypertrophy in the center of the thighbone as in Reference Example 1, whereas (d) the mouse with SIK3 Tg SIK3$^{-/-}$ genotype showed no inhibition of chondrocyte hypertrophy. Consequently, it was clear that the function of SIK3 was rescued.

The above results revealed that the inhibition of chondrocyte hypertrophy was brought by the functional deficiency of SIK3.

Reference Example 3

Observation of Growth Plate of Knee Joint of SIK3 Transgenic Mice

Three-, six-, and eight-month-old SIK3 Tg mice and wild-type (WT) mice were euthanized by carbon dioxide inhalation and dissected for harvesting the forelimbs and hindlimbs. The harvested limbs were fixed in formalin and then decalcified in EDTA. Next, sections were produced and stained in the same manner as in Reference Example 1.

Figure 6:
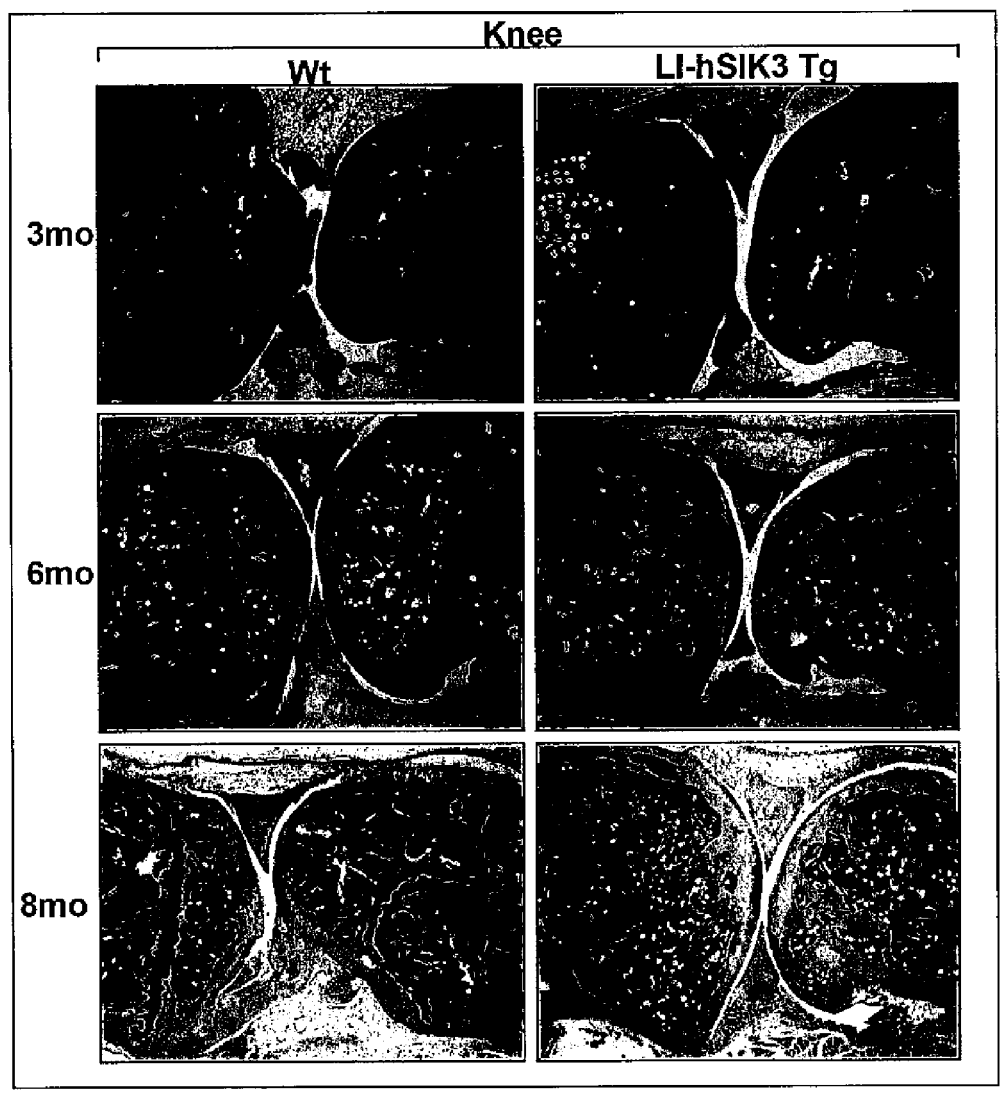
FIG. 6 shows histologically stained sections including the knee joint of 3-, 6-, and 8-month-old SIK3 gene transgenic mice and wild-type mice.

The obtained specimens were observed under an optical microscope. FIG. 6 shows histologically stained sections including the knee joint of each of the 3-, 6-, and 8-month-old mice. The left is the wild-type mice ("Wt" in the figure) and the right is the SIK3 Tg mice ("LI-hSIK3 Tg" in the figure). As is apparent from FIG. 6, the growth plate was observed in both of the wild-type mice and the SIK3 Tg mice at 3 months old, but the growth plate disappeared from the SIK3 Tg mice at 6 and 8 months old, while the growth plate in the wild-type mice was observed at 6 and 8 months old.

From the above results, enhancement of the function of SIK3 was considered to accelerate chondrocyte hypertrophy and endochondral ossification.

Example 1

Screening Method

Into HEK293 cells, a reporter vector GAL4-Luc (firefly luciferase: pTAL-5XGAL4 (150 ng)), an endogenous reporter vector (Renilla luciferase: pRL-Int (−) (30 ng)), a vector with or without the expression of TORC (pM-TORC2 or pM only (50 ng)) and a vector with or without the expression of SIK3 (pTarget-SIK3 or pTarget only (50 ng)) were introduced using Lipofectamine 2000. Twenty-four hours later, a test substance was added and the cells were further treated for 6 hours. The measurement of the reporter activity was performed using Dual-Luciferase assay kit made by Promega. As the test substance, staurosporine (STS) or a SIK2 inhibitor (Compound C) was used. As a control, DMSO alone was added. The schematic view of the screening system is shown in FIG. 6.

Figure 7:
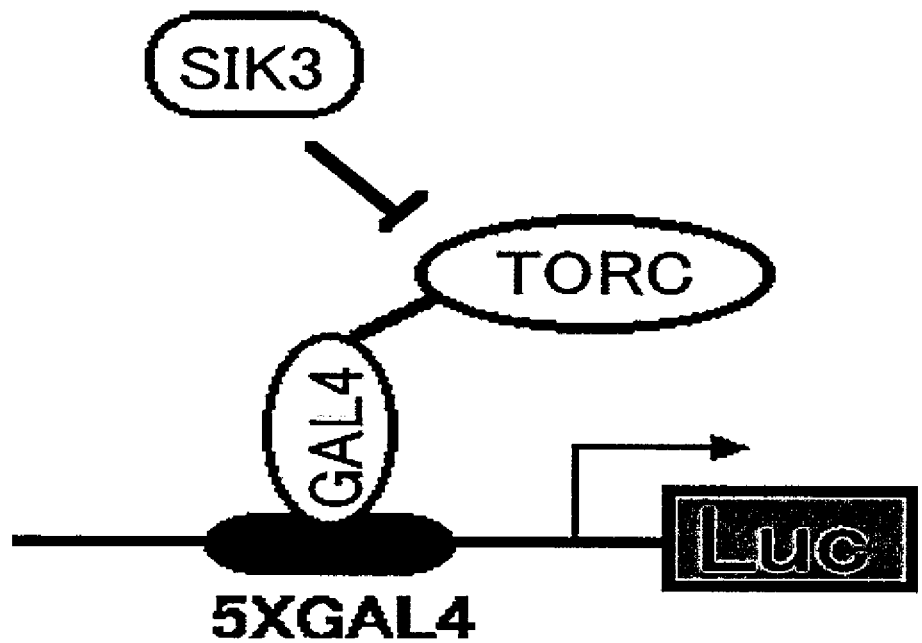
FIG. 7 is a schematic view of the screening system of Example 1.
Figure 8:
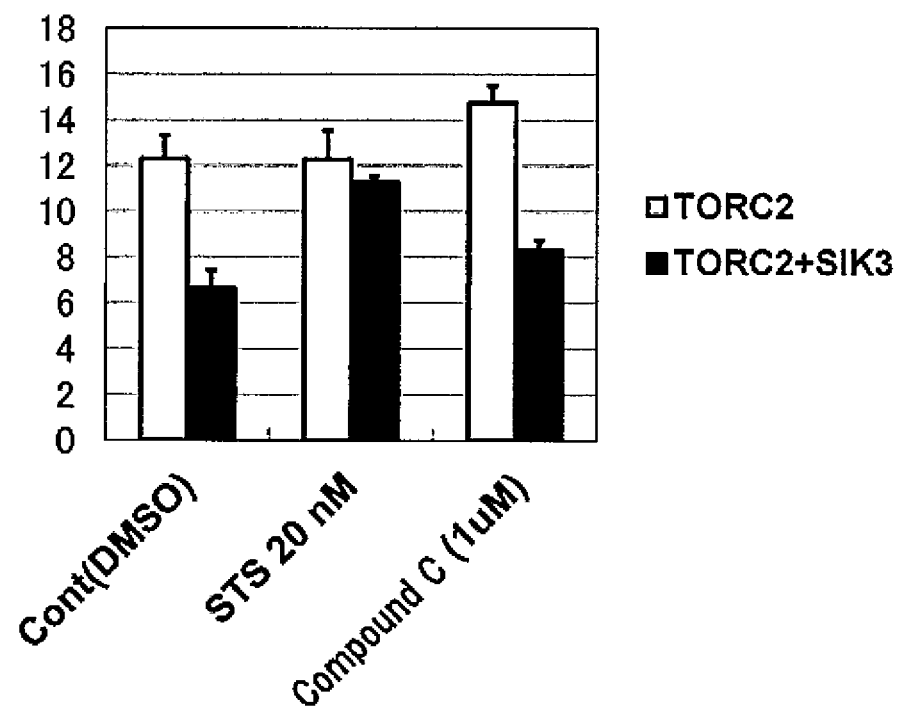
FIG. 8 is a chart showing the results of screening of test substances by the screening system of Example 1.

The results are shown in FIG. 7. In FIG. 7, the vertical axis represents the activity of TORC2, which is the activity of pM-TORC2 that was calculated by dividing the firefly luciferase activity by the Renilla luciferase activity and is expressed as a multiple of the activity of pM. The white bars and the black bars represent the activities of TORC2 with the absence and presence of SIK3, respectively. A large difference between the white bar (with the absence of SIK3) and the black bar (with the presence of SIK3) indicates that the activity of SIK3 is large, and a small difference between the white bar (with the absence of SIK3) and the black bar (with the presence of SIK3) indicates that the activity of SIK3 is inhibited. As is apparent from FIG. 7, the inhibiting activity of staurosporine (STS) on SIK3 was detected.

The present invention is not limited to each of the embodiments and Examples described above and various modifications thereof are possible within the scope of the claims. Embodiments obtainable by appropriately combining the technical means disclosed in the different embodiments are also included in the technical scope of the present invention. The entire contents of the scientific literature and patent literature that have been described in the specification are incorporated herein by reference.

The invention claimed is:

1. A screening method for a substance having an effect of increasing cartilage volume and/or an effect of reducing the speed of chondrocyte differentiation, the method comprising contacting (a1) a mammalian cell expressing endogenous salt-inducible kinase 3 SIK3, (b1) a cell into which a vector containing a reporter gene fused downstream of a mammalian SIK3 promoter has been introduced, or (c1) a mammalian SIK3 protein and its substrate, with a test substance, measuring (a2) the amount of SIK3 protein or mRNA in the mammalian cell, (b2) the promoter activity of mammalian SIK3 in the cell carrying the vector, (c2) the binding of the mammalian SIK3 protein to its substrate or (c2') the phosphorylation of the substrate for the mammalian SIK3 protein, and selecting a test substance (a3) decreasing the amount of the SIK3 protein or mRNA, (b3) decreasing the promoter activity of SIK3, (c3) decreasing the binding of the SIK3 to its substrate, or (c3') decreasing the phosphorylation of the substrate for SIK3, compared with a control group free from contact with the test substance.

2. The screening method according to claim 1, wherein the measuring step further comprises measuring the level of activation of a substrate for SIK3.

3. The screening method according to claim 2, wherein the measurement of the level of activation of a substrate for SIK3 is performed by measuring the amount of reporter gene product in a cell containing a reporter gene linked to a promoter to be activated by the substrate for SIK3, a SIK3 expression vector, and a SIK3 substrate expression vector.

4. The screening method according to claim 3, wherein the promoter to be activated by the substrate for SIK3 is 5×GAL4, and the substrate for SIK3 is fused with GAL4.

5. The screening method according to claim 2, wherein the substrate for SIK3 is TORC or TORC2.

6. The screening method according to claim 1, wherein the substance having an effect of increasing cartilage volume and/or an effect of reducing the speed of chondrocyte differentiation is selected from the group consisting of therapeutic agents for osteoarthritis, cartilage injury, and chondrodysplasia.

7. The screening method according to claim 1, wherein the substance having an effect of increasing cartilage volume and/or an effect of reducing the speed of chondrocyte differentiation has an effect of thickening of articular cartilage.

8. The screening method according to claim 1, wherein the test substance is selected from the group consisting of a nucleic acid, a peptide, a protein, a non-peptidic compound, a synthetic compound, a fermentation product, a cell extract, a cell culture supernatant, a plant extract, a mammalian tissue extract, and plasma.

* * * * *

SEQUENCE LISTING

```
<160> NUMBER OF SEQ ID NOS: 8

<210> SEQ ID NO 1
<211> LENGTH: 1873
<212> TYPE: DNA
<213> ORGANISM: Homo sapiens

<400> SEQUENCE: 1
aaaacaaaaa cccaaaaact gcagctgtga agcccagcac caaagttata gtccctgcta      60
gaggcagctg agagccatga agtgatagga gaggcaggtc acacccatc atttatctgg     120 gatggaatga gctcagctga tgaaagggct taaccaatgc aagaagccaa ggcccacttc     180
attcttatct ttagttgcta ataagggagc caattagtgt taattgtgtt ggcagtttgg     240
aacagctacc agggaataga tccaagacca ttgtgggatg accctctgt cccatcttaa     300 gtcccagcca ttactcatgg ttggatagg aattggagca ccaggaggtg ttctttggtc     360
agcgagtaaa cacgagttat ccttccacac atttacagtg ccctgggtgt cagtttttaa     420
tactgtgcat gcagtgacct cacaatacag ttctaccatt gagagagaca tagatatgga     480
tggatcagga ctagtccaaa ggaatacatt ttaacattgg aatattcaca atcttccctc     540
ctttccaccc agcctgccaa agactatttt gttgacagtc tgatttccta cctgcaaccc     600
tcacctaaag cagctaagtt aatctatta ataaagggaa gggggagagag gaggaggaag     660 cctgggagct atgaaggatg caggtaatag gcaagggaag aaaaagagat atgaaattgc     720
```

```
tggagttatt aacttgatga ccctcaatgt cctcggagag tcactaggaa ggatggaatt      780
tttattattt acttatttat tttgcttaac cgactgttgt ttaaacacga cgtggttcat      840
tggacaatgc gcaccactgc ttcatcaggg ttatacaagc aacagaaata gtatgtaggc      900
actctgacag acatccctgt agaattgttc agagatgggg gtggtaggaa ggaaaatgac      960
gtaccttctt tggctgtcac ccacccaatg actggaatgc ctgtttggac tggcttgtcc     1020
gcccttgaac acgcaaatcc tagtttcccc attctcctat attcggtgac aattaggttg     1080
actgtgcagg gtgagctgga ttttgtaaga ggaaggaatt ttaccgaaga attcccctgc     1140
gttgttacca acttggttac agttgcttca agagtgtagc tattcctgca tttgtggcct     1200
caagggctaa agtgggacaa cgctggtatt tttggtgatg aggaaacact ttttttttgt     1260
taagggaggt tgggtgatcg ttgaactggg acagaggtca cagcagaggt cacattggcg     1320
attcgagcgg cggtgggggg ttggctttgg gtcgggcatc ctgcgccccc cactcgggaa     1380
aggtggcgga gacttcgagg ttgggggccc atcgaaggtt cccaccgcca gctcccggag     1440
gggggcaccc gggagccagc gcctcaggaa ccggggccca cgcgggaagg tcgagcccgc     1500
cggtgaggtc acggttgcca tggctccggg cagtgacgcg cgtcggcacg tgacccgcgg     1560
ttgccatgga gccgggcgcc ggtcggcgaa agcgccccgc ctccccgagt gacgtccgcg     1620
gccccccctt tcccgccccc ccttgccccc tccccgagc cggctccccg cggccccgga     1680
ggtttcactg cacaacaaga tggcggcggc ggcggcgagc ggagctggcg gggctgccgg     1740
ggccgggact gggggagccg ggccgcgggg ccgcctgctg cctccgcccg cgccggggtc     1800
cccagccgcc cccgctgccg tgtccctgc ggccggccag ccgcgtcccc cagccccggc     1860
ctcccgcgga ccc                                                       1873

<210> SEQ ID NO 2
<211> LENGTH: 2610
<212> TYPE: DNA
<213> ORGANISM: Mus musculus

<400> SEQUENCE: 2
ttatctggct atcctatact cactgctagg gaaccagcag gataggtctc tttggaaatt       60
aaagcaatgc tccattttcc tagctcctcc tcaaggcttt cttgaagtga ggggtggggt      120
gggggagtga tacaatgaga atttgaataa gaggtgcagc tcagttggta gagtgagtgc      180
acagtaaagc attatcacgg agccccgagt ttgatcttca gcactgcatg agataggtca      240
ggacattgct gggcagtggt ggcgcacgcc tttaatccca gcactcgttg gtgggagagg      300
caggcggatt tctgagttcg aggccaggct ggtctacaga gtgagttcca ggacagccag      360
ggccatatag agaaccctg tctcgaaaaa ccgaaaaaac aaaacaaaac aaaacaaaaa      420
caaaaacaaa aaacccaaa aaaagacagg tcgagcacac ctgtaactcc tgtatttggg      480
aagtggaagc agagagatca cagattcaag gttgtccttg gttacccaga acttctgaaa      540
tcagccaggg caaaatgaaa cttttgcttag ctgggtgtgg gtgtggtagc tacaagcctt      600
taatccagca caggggaagc agaggcaggt ggatctgtgt gtttgaggct ggcttgatta      660
cgtattcagt tccaggatat ccaggactac atggagagag actgtctcag agagagagag      720
agagagagag agagagagag agagagaaag aagaagaaga agaagaagaa gaagagagaa      780
tttgatcaaa acaaacaaat tttccaatta tgtctaaatg tctaagagtg aagacactc      840 tgggtgcaca gcctagacaa gagtggcttc agtactgatt ctaagccttc cagagagaaa      900
gcttgttttt ctttgtctta ccaggagagc tccccacctc cagggagatg gtaaacctca      960
```

```
ttctgaggtc cagcccctaa gttattggct ttgctagatt ccagcaaggg ccatgaagtt      1020
gtaagggcca cacccaatca ttcatctcag atttcgtaat ctcacttgat gaataggttt      1080
aagcagccta agaagcaagg tccacttcat ccctgtcttt atttgcttgt aaaggagcca      1140
attagtgtta attgtgctgg caatttgaaa tagccaccag ggaactgatt caaggcagtt      1200
gtgggatgac ccctctgtcc catcctagac ccagccatta cttatgtcac atgggggaa      1260 tcagaacatt gggaaagac ctgtggtcag aaagggtaag catgtatttc ctttctcaca      1320
tacccagtga cctggatgtc acttttttgat actgcacaga gatgtgacaa tactcctgtg      1380
ccatggaggg agatacaggt gtgggtagaa tagcactgga tacatgagat acaattatat      1440
agaggaatgc acacagcctt cttccttcct tttctaacgg accaaaggct atctctcctt      1500
tacagcccaa tttcctatcc ccaccagagg cagataaatc aatctactta ataaggaagg      1560 aggagggga gaggctcagt tacagcccag gatgtggaat gtcagataac aggagggaag      1620
aaagagggat atgagttta ttgcagggt tattaatttg atcactctta atgtccttgg       1680
agagtcatta gtagggatgg aatttatatt agttactcgt tttgcttaac ggattgctca      1740
tctttaagca tgacgtggcc ctgaatgcaa cacacttcac cagtactaac ccagcaacag      1800
aaaacgagtg aagagattct gaccaactgg ctggagaatt gttccgagtc aggggtggca      1860
ggaaggaaaa tgacggtcct tttctggccc tcacccaccc aaagactgga acgcatgttt      1920
gggatgggtt caacatcctt gaatatgcaa actctaattt ccgcactctt ctgtgttcga      1980
tgacttatta gattgattgt acgaagtgag ctgggctttg taagagttttt tgctgaacaa      2040 ttcccctgcc ttgctaccaa cttggttaca gttgcttaaa tactgtagct attcctgcct      2100
ctgtggcctc cagggctaaa gtgggacaag gctggtattt tggtgacga ggaaatcctt       2160 ttaagggagg tttggtgatg actgaactgg gacacaggtc ggagcaggga tcccatcagc      2220
gaaccagggg ccatcgggag tctggttctg gggtctcccc atctcatatc cctacctcgc      2280
taggcgcggc ggaagcttag aagttgctgc tgaccctcga cgttttcaat gcctgttccc      2340
cagagggggg cactagggag ccggcgcctc aggaacaggg acccacgcgg gaaggtcgag      2400
ctcgcccggt gaggtcacgg ttgccatggc ttcgggcagt gacgcgcgtc cgcacgtgac      2460
gcgcggttgc catggcgtcg ggcgcccggc ggcgcgggag ccccgcctcc cggagtgacg      2520
tctgtcggca accccctct ttcggccccc ccgcgccccc tcccccccgg ccggctcccc        2580
gcggccccgg aggtttcact gcacaacaag                                       2610
```

<210> SEQ ID NO 3
<211> LENGTH: 693
<212> TYPE: PRT
<213> ORGANISM: Homo sapiens

<400> SEQUENCE: 3

Met Ala Thr Ser Gly Ala Asn Gly Pro Gly Ser Ala Thr Ala Ser Ala
1               5                   10                  15

Ser Asn Pro Arg Lys Phe Ser Glu Lys Ile Ala Leu Gln Lys Gln Arg
            20                  25                  30

Gln Ala Glu Glu Thr Ala Ala Phe Glu Glu Val Met Met Asp Ile Gly
        35                  40                  45

Ser Thr Arg Leu Gln Ala Gln Lys Leu Arg Leu Ala Tyr Thr Arg Ser
    50                  55                  60

Ser His Tyr Gly Gly Ser Leu Pro Asn Val Asn Gln Ile Gly Ser Gly
65                  70                  75                  80

-continued

```
Leu Ala Glu Phe Gln Ser Pro Leu His Ser Pro Leu Asp Ser Ser Arg
                85                  90                  95
Ser Thr Arg His His Gly Leu Val Glu Arg Val Gln Arg Asp Pro Arg
            100                 105                 110
Arg Met Val Ser Pro Leu Arg Arg Tyr Thr Arg His Ile Asp Ser Ser
        115                 120                 125
Pro Tyr Ser Pro Ala Tyr Leu Ser Pro Pro Glu Ser Ser Trp Arg
    130                 135                 140
Arg Thr Met Ala Trp Gly Asn Phe Pro Ala Glu Lys Gly Gln Leu Phe
145                 150                 155                 160
Arg Leu Pro Ser Ala Leu Asn Arg Thr Ser Asp Ser Ala Leu His
                165                 170                 175
Thr Ser Val Met Asn Pro Ser Pro Gln Asp Thr Tyr Pro Gly Pro Thr
            180                 185                 190
Pro Pro Ser Ile Leu Pro Ser Arg Arg Gly Gly Ile Leu Asp Gly Glu
        195                 200                 205
Met Asp Pro Lys Val Pro Ala Ile Glu Glu Asn Leu Leu Asp Asp Lys
    210                 215                 220
His Leu Leu Lys Pro Trp Asp Ala Lys Lys Leu Ser Ser Ser Ser Ser
225                 230                 235                 240
Arg Pro Arg Ser Cys Glu Val Pro Gly Ile Asn Ile Phe Pro Ser Pro
                245                 250                 255
Asp Gln Pro Ala Asn Val Pro Val Leu Pro Pro Ala Met Asn Thr Gly
            260                 265                 270
Gly Ser Leu Pro Asp Leu Thr Asn Leu His Phe Pro Pro Leu Pro
        275                 280                 285
Thr Pro Leu Asp Pro Glu Glu Thr Ala Tyr Pro Ser Leu Ser Gly Gly
    290                 295                 300
Asn Ser Thr Ser Asn Leu Thr His Thr Met Thr His Leu Gly Ile Ser
305                 310                 315                 320
Arg Gly Met Gly Leu Gly Pro Gly Tyr Asp Ala Pro Gly Leu His Ser
                325                 330                 335
Pro Leu Ser His Pro Ser Leu Gln Ser Ser Leu Ser Asn Pro Asn Leu
            340                 345                 350
Gln Ala Ser Leu Ser Ser Pro Gln Pro Gln Leu Gln Gly Ser His Ser
        355                 360                 365
His Pro Ser Leu Pro Ala Ser Ser Leu Ala Arg His Val Leu Pro Thr
    370                 375                 380
Thr Ser Leu Gly His Pro Ser Leu Ser Ala Pro Ala Leu Ser Ser Ser
385                 390                 395                 400
Ser Ser Ser Ser Ser Thr Ser Ser Pro Val Leu Gly Ala Pro Ser Tyr
                405                 410                 415
Pro Ala Ser Thr Pro Gly Ala Ser Pro His His Arg Arg Val Pro Leu
            420                 425                 430
Ser Pro Leu Ser Leu Leu Ala Gly Pro Ala Asp Ala Arg Arg Ser Gln
        435                 440                 445
Gln Gln Leu Pro Lys Gln Phe Ser Pro Thr Met Ser Pro Thr Leu Ser
    450                 455                 460
Ser Ile Thr Gln Gly Val Pro Leu Asp Thr Ser Lys Leu Ser Thr Asp
465                 470                 475                 480
Gln Arg Leu Pro Pro Tyr Pro Tyr Ser Ser Pro Ser Leu Val Leu Pro
                485                 490                 495
```

```
Thr Gln Pro His Thr Pro Lys Ser Leu Gln Gln Pro Gly Leu Pro Ser
            500                 505                 510

Gln Ser Cys Ser Val Gln Ser Ser Gly Gly Pro Pro Gly Arg Gln
    515                 520                 525

Ser His Tyr Gly Thr Pro Tyr Pro Pro Gly Pro Ser Gly His Gly Gln
530                 535                 540

Gln Ser Tyr His Arg Pro Met Ser Asp Phe Asn Leu Gly Asn Leu Glu
545                 550                 555                 560

Gln Phe Ser Met Glu Ser Pro Ser Ala Ser Leu Val Leu Asp Pro Pro
                565                 570                 575

Gly Phe Ser Glu Gly Pro Gly Phe Leu Gly Gly Glu Gly Pro Met Gly
            580                 585                 590

Gly Pro Gln Asp Pro His Thr Phe Asn His Gln Asn Leu Thr His Cys
            595                 600                 605

Ser Arg His Gly Ser Gly Pro Asn Ile Ile Leu Thr Gly Asp Ser Ser
            610                 615                 620

Pro Gly Phe Ser Lys Glu Ile Ala Ala Leu Ala Gly Val Pro Gly
625                 630                 635                 640

Phe Glu Val Ser Ala Ala Gly Leu Glu Leu Gly Leu Gly Leu Glu Asp
                645                 650                 655

Glu Leu Arg Met Glu Pro Leu Gly Leu Glu Gly Leu Asn Met Leu Ser
            660                 665                 670

Asp Pro Cys Ala Leu Leu Pro Asp Pro Ala Val Glu Glu Ser Phe Arg
            675                 680                 685

Ser Asp Arg Leu Gln
    690

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
gctaccaact tggttacagt tgct                                          24

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
aaaacgtcga gggtcagcag caacttctaa                                    30

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6
acgagactag tgagacgtgc tacttccatt                                    30

<210> SEQ ID NO 7
<211> LENGTH: 19
<212> TYPE: DNA
```

```
<213> ORGANISM: Artificial Sequence
<220> FEATURE:
<223> OTHER INFORMATION: Primer

<400> SEQUENCE: 7
gatgtcggat gcagttctc                                             19

<210> SEQ ID NO 8
<211> LENGTH: 26
<212> TYPE: DNA
<213> ORGANISM: Artificial Sequence
<220> FEATURE:
<223> OTHER INFORMATION: Primer

<400> SEQUENCE: 8
atgtctgtaa tacacgtaga tggata                                     26
```